United States Patent [19]

Mangus

[11] Patent Number: 4,996,800
[45] Date of Patent: Mar. 5, 1991

[54] CAUTERY TIP CLEANER

[76] Inventor: Donald J. Mangus, 500 Cohasset Rd. Suite 27, Chico, Calif. 95926

[21] Appl. No.: 247,763

[22] Filed: Sep. 21, 1988

[51] Int. Cl.[5] .......................... B24B 1/00; B24D 15/00
[52] U.S. Cl. .................................... 51/281 R; 51/358; 51/391; 51/404; 51/285; 15/210 B; 15/218.1
[58] Field of Search ................. 51/16, 17, 214, 181 R, 51/281 R, 285, 358, 391, 394, 395, 397, 398, 400, 401, 404, 407; 15/210 B, 210 R, 218.1, 218; 128/303.13, 303.14, 303.17, 303.18

[56] References Cited

U.S. PATENT DOCUMENTS

| | | | |
|---|---|---|---|
| Re. 29,678 | 6/1978 | Antonini et al. | 206/571 |
| 1,652,875 | 12/1927 | Rein et al. | 15/210 B |
| 2,699,565 | 1/1955 | Brough | 15/236 |
| 3,094,730 | 6/1963 | Schwarz | 15/210 |
| 3,862,522 | 1/1975 | Mednick | 51/404 X |
| 3,982,357 | 9/1976 | Eldridge et al. | 51/181 |
| 3,998,012 | 12/1976 | Ness | 51/401 X |
| 4,011,693 | 3/1977 | Eldridge, Jr. et al. | 51/354 |
| 4,103,388 | 8/1978 | DeVitis | 15/210 B |
| 4,164,054 | 8/1979 | Hanson et al. | 15/210 B |
| 4,361,926 | 12/1982 | Brush et al. | 15/236 R |
| 4,506,404 | 3/1985 | Clay | 15/244 |
| 4,543,751 | 10/1985 | Alikhan | 51/358 X |
| 4,547,923 | 10/1985 | DeVries et al. | 15/104 |
| 4,704,760 | 11/1987 | Grieshaber | 15/218.1 |

FOREIGN PATENT DOCUMENTS 4361 1/1983 Japan .................................... 51/395

*Primary Examiner*—Robert P. Olszewski
*Attorney, Agent, or Firm*—Limbach, Limbach & Sutton

[57] ABSTRACT

An inexpensive, lightweight apparatus and method is provided for removing coagulum and other debris from the tip of cautery blades and needles during use. The cleaner comprises a pad having a lower compressible portion and an upper fibrous abrasive portion which is mounted to a non-compressible base. The apparatus can be attached to a surgical drape or other accessible surface to permit cleaning using only one hand to manipulate the cauterizing instrument. The upper abrasive portion contains one or more elongated slits each of which has opposing abrasive walls and an abrasive floor. Cautery blades are cleaned by pressing the edge of a blade down between two opposing walls and drawing the blade toward the opposite end of the elongated slit. Cautery needles are cleaned by pushing them into, and then withdrawing them from, the upper abrasive portion.

14 Claims, 1 Drawing Sheet

CAUTERY TIP CLEANER

TECHNICAL FIELD

The present invention relates to medical devices. In particular, the present invention relates to a device for cleaning cauterizing instrument tips.

BACKGROUND ART

Cauterizing instruments are commonly used in surgery for making and cauterizing incisions and wounds. Such cauterizing instruments are typically used with a flat blade tip or a needle tip, depending upon the extent of cauterizing required. Such flat blade tips and needle tips are available in varying sizes.

As such cauterizing instruments are used, coagulated blood, small bits of flesh and other debris adhere to the tip, causing a degradation in the current flow and efficiency of the cauterizing process, and obstructing the surgeon's view of the tip of the instrument. Thus, it is necessary to periodically remove the coagulum and debris from the tip during use of the cauterizing instrument.

Coagulum and debris can be removed from a cautery tip by wiping the tip repeatedly on a piece of sandpaper which is taped or pinned within reach of the surgeon, typically on the patient's surgical drape. This method usually requires that the surgeon twist or rotate his wrist as he cleans the cauterizing instrument to insure that all surfaces of the cautery tip are sufficiently cleaned. This method is disadvantageous because it is time consuming and takes the attention of the surgeon away from the patient and directs it to the cleaning process. Further, with sandpaper alone there may be a danger of accidental needle sticks to the patient if the sandpaper is accidentally perforated during the cleaning process.

Other, more complex devices for cleaning cautery tips are also found in the art. For example, U.S. Pat. No. 4,506,404 provides a disposable sponge for cleaning surgical instruments. U.S. Pat. No. 4,361,926 to Brush provides a cautery tip cleaner which is attached to the cauterizing instrument for moving over the cautery tip for removing the coagulum. However, these devices are disadvantageous because they require two-handed operation and take the attention of the surgeon away from the patient.

One-handed devices for cleaning cautery tips are also known. For example, U.S. Pat. Nos. 4,011,693 and 3,982,357 disclose cautery tip cleaners having confronting abrasive strips urged into mutual engagement by magnetic force. Flat cautery tips are cleaned by drawing them between the confronting abrasive strips. U.S. Pat. No. 4,547,923 discloses a compressed coil spring in which a flat cautery blade is cleaned by drawing it through two adjacent individual coils. The problem with these devices is that they are relatively complex and correspondingly expensive to produce, and they do not provide an efficient means for cleaning cautery needles.

Therefore, the need exists for a simple and inexpensive apparatus for efficiently and quickly cleaning both cautery needles and blades by a one-handed operation, and in which the possibility of accidental needle sticks to the patient during the cleaning operation is eliminated.

SUMMARY OF THE INVENTION

The present invention provides a lightweight, simple, inexpensive cautery tip cleaner which efficiently and quickly cleans both cautery needles and cautery blades by a one handed operation.

In one embodiment, the present invention provides a compressible pad having a thick, fibrous abrasive portion on top and a hard base attached to the bottom. The fibrous abrasive portion contains one or more elongated cuts or slits for cleaning cautery blades, with the cuts partially penetrating the fibrous abrasive portion to a depth which is less than the thickness of the abrasive portion to form two opposing abrasive walls and an abrasive floor. Cautery blades are cleaned by pressing them down between opposing abrasive walls and against the abrasive floor, drawing them through the elongated cuts in the surface of the compressible pad. Cautery needles are cleaned by plunging them through the fibrous abrasive portion. The cautery tip cleaner can be attached to a surgical drape or other surface within easy reach of the surgeon by means of an adhesive strip or patch attached to the underside of the hard base.

In another embodiment, the present invention provides a pad of fibrous, abrasive material mounted on a compressible sponge pad of similar size and shape which is mounted on a hard base. The fibrous abrasive pad contains one or more elongated cuts along its top surface which penetrate the surface without penetrating through the bottom of the fibrous abrasive pad.

In yet another embodiment, the present invention uses a hard base for the compressible pad which includes holes for using fasteners, such as pins, for attaching the cautery tip cleaner to a surgical drape or other surface within easy reach of the surgeon.

Other embodiments and modifications will become apparent from the detailed description set forth below.

BRIEF DESCRIPTION OF THE DRAWINGS

A better understanding of the invention and its advantages will be apparent from the detailed description taken in conjunction with the accompanying drawings in which.

DETAILED DESCRIPTION

Figure 1:
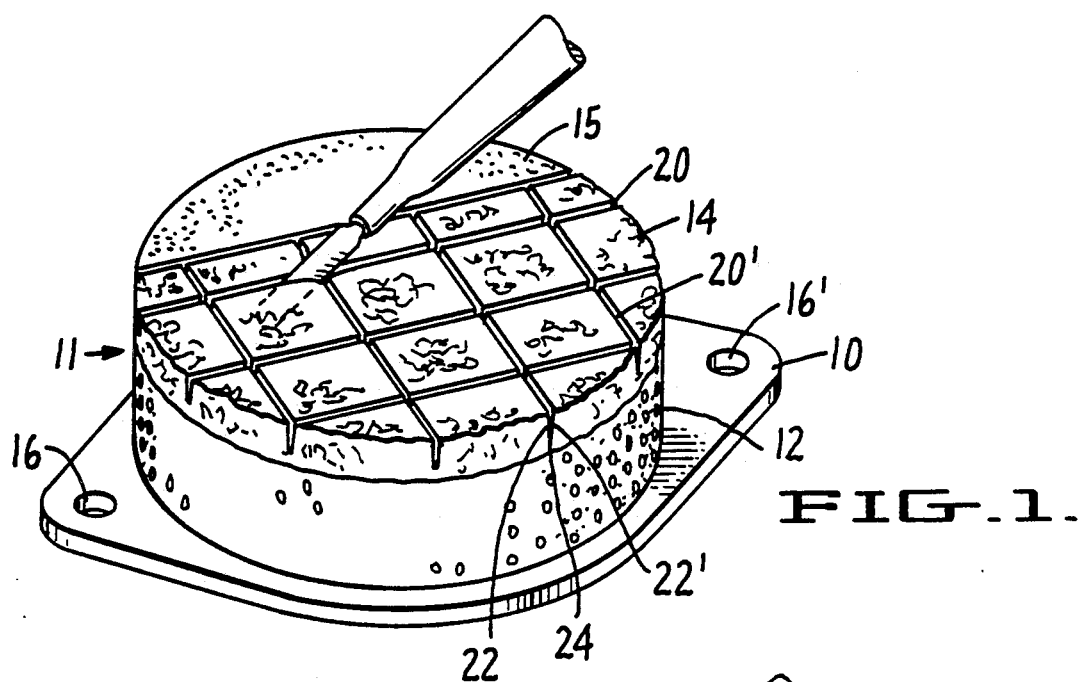
FIG. 1 is a perspective top external view of a cautery tip cleaner of the present invention.
Figure 2:
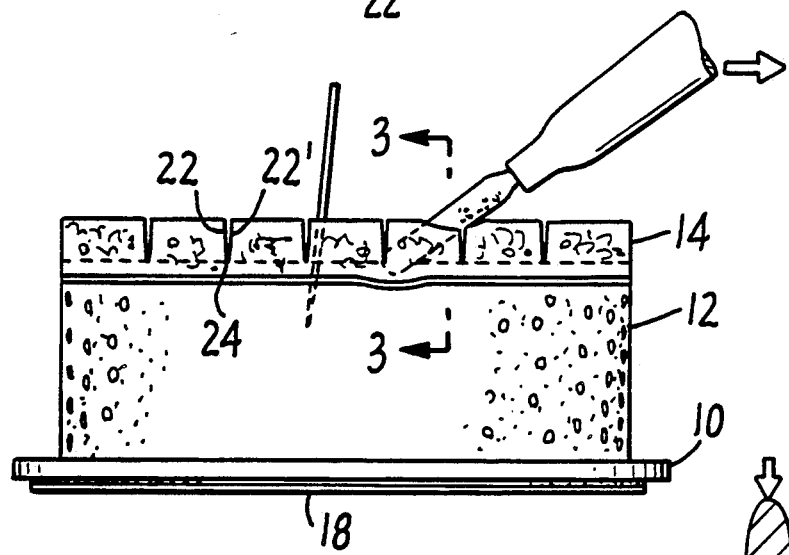
FIG. 2 is a side view of a cautery tip cleaner of the present invention.

FIGS. 1 and 2 show a cautery tip cleaner of the present invention. The cautery tip cleaner comprises a base 10 on which is mounted a pad 11 having a compressible portion 12 and a fibrous, abrasive portion 14.

Base 10 is preferably constructed from a hard, generally noncompressible material such as hard plastic or metal. Base 10 is most preferably resistant to penetration by cautery needles. Base 10 can also be adapted for mounting the cautery tip cleaner to a surface within easy reach of a surgeon or other user, such as a surgical drape, by providing an adhesive strip or patch 18 on the bottom of the base 10 for attaching the cautery tip cleaner to the surface. In addition, or in lieu of the adhesive 18, holes 16, 16' may be provided in the base for pinning the cautery tip cleaner to the surgical drape.

Abrasive portion 14 is constructed from a fibrous abrasive material such as 3M's SCOTCHBRITE® cleaning and polishing material. Abrasive portion 14 is provided with one or more elongated cuts 20, 20' which penetrate the surface of the abrasive portion to a depth sufficient to permit the cleaning of the tip of the cautery blade without exceeding the thickness of the abrasive portion. Thus, the fibrous abrasive portion should be sufficiently thick to provide in each elongated cut 20, 20' opposing abrasive surfaces 22, 22' for cleaning the sides of a cautery blade and an abrasive floor 24 for cleaning the edge of a cautery blade. Optionally, a portion of the top surface of abrasive portion 14 can include coarse sandpaper 15 for removing the most resistant coagulum from the cautery tip.

Compressible portion 12 is preferably constructed from sponge, or other similar elastically compressible material. In this embodiment pad 11 is formed by attaching a pad of fibrous abrasive material of the desired thickness on top of a similarly sized pad of sponge. Attachment can be made using any suitable adhesive. Alternatively, compressible portion 12 may consist of an additional thickness of fibrous abrasive material underlying abrasive portion 14. Such a pad can be constructed from a single thickness or piece of fibrous, abrasive material divided into an upper portion or zone for cleaning and a lower portion or zone for providing compression if the fibrous, abrasive material is sufficiently elastically compressible so that the downward pressure of the cautery blade on the floor 24 of an elongated cut 20 in the upper portion will compress the underlying fibrous material in the lower portion against the hard base 10, deforming the floor 24 and drawing the opposing abrasive surfaces 22, 22' down and against each side of the cautery blade. Further, by making the pad from one piece of fibrous, abrasive material the production costs involved in assembling the cautery tip cleaner should be reduced.

The preferred dimensions of the pad 11 are from about 1.25 to about 1.5 inches in height and about 3 inches in diameter. This size makes it easy for the user to clean cautery tips quickly with minimal distraction from the operating field. Although the general shape of the pad 11 is shown as being round, one skilled in the art will recognize that many different shapes can be used including oval, rectangular, pyramidal, and polygonal.

Figure 3:
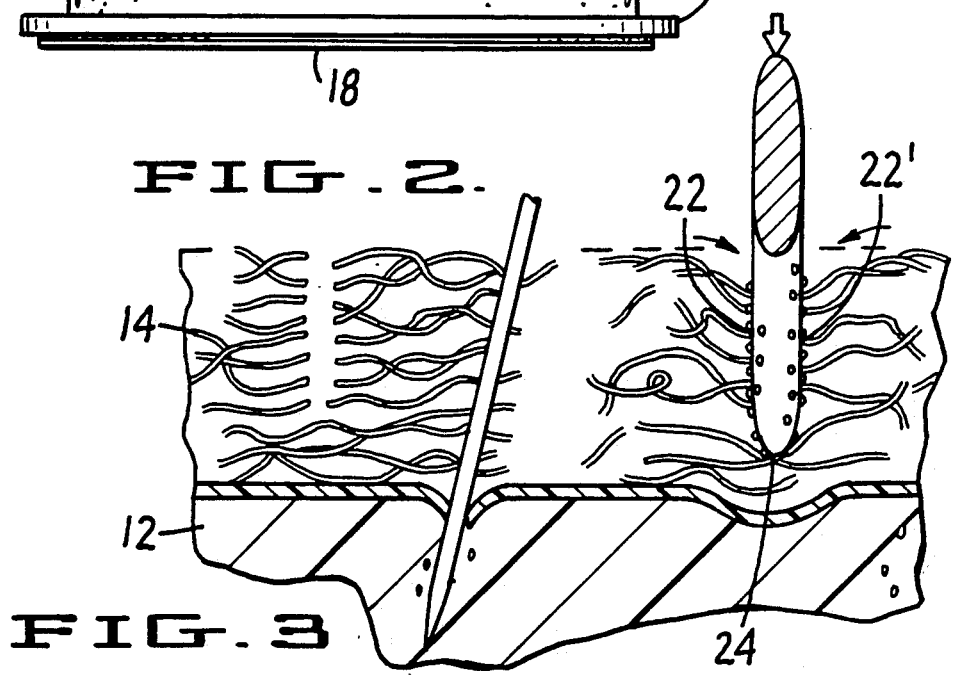
FIG. 3 is a sectional side view of a cautery tip cleaner of the present invention taken along line 3—3 of FIG. 2.

As shown additionally in FIG. 3, to clean a cautery blade, the blade is pressed down into an elongated cut 20 and drawn through the cut 20 towards the other end of the elongated cut 20. As the flat edge of the blade is pressed against floor 24, the underlying material compresses against the hard base 10 and the floor 24 deforms, drawing the opposing abrasive surfaces 22, 22' down and together against the sides of the blade. The dual motion of downward compression and lateral movement through the elongated cut 20 efficiently and quickly removes coagulum and debris from a cautery blade and can be easily accomplished using only one hand.

To clean a cautery needle, the user simply plunges the needle through the abrasive portion 14 and then retracts it. Because the abrasive portion 14 is a fibrous abrasive which surrounds and scours off all sides of the needle as the needle penetrates the abrasive portion 14, no rotation of the needle is required; therefore the surgeon need not rotate or twist his wrist during the cleaning process. In the preferred embodiment, where compressible portion 12 is constructed from sponge, the scouring action of the abrasive portion 14 is supplemented by the wiping action of the compressible portion 12. Because the compressible portion 12 is mounted on a hard base 10, there is no danger of a needle accidentally penetrating the compressible portion 12 and puncturing the patient.

One skilled in the art will recognize at once that it would be possible to construct the various components of the present invention from a variety of materials which are sterilizable. The present invention can be constructed so that it is either reusable or disposable after a first use. While the preferred embodiment and alternative variations have been described in detail and shown in the accompanying drawings, it will be evident that other and various further modifications are possible without departing from the scope of the invention as embodied in the claims.

I claim:

1. A surgical cautery tip cleaner for cleaning both surgical cautery needles and surgical cautery blades comprising:
   a hard base having a bottom surface and a top surface, said base being resistant to penetration by needles or other sharp objects;
   a cleaning pad mounted on the top surface of the hard base and having an upper fibrous abrasive portion and a lower compressible portion, said lower compressible portion being located between the upper abrasive portion and the hard base, said upper fibrous abrasive portion having a top surface and a bottom surface and containing one or more elongated cuts which penetrate the top surface of the upper fibrous abrasive portion, said elongated cuts having sufficient depth to clean the tips of cautery blades without penetrating the bottom surface of the upper fibrous abrasive portion;
   said base and said cleaning pad being constructed from materials suitable for sterilizing to permit the cautery tip cleaner to be used in surgery or for other medical procedures.

2. The cautery tip cleaner of claim 1 additionally comprising a means for attaching the base to a surface within easy reach of a user.

3. The cautery tip cleaner of claim 2 in which said means for attaching the base to a surface comprises adhesive attached to the bottom surface of the hard base.

4. The cautery tip cleaner of claim 1 in which the compressible portion comprises sponge.

5. The cautery tip cleaner of claim 1 wherein the fibrous abrasive portion comprises SCOTCHBRITE ®.

6. The cautery tip cleaner of claim 1 wherein the base is constructed from a hard plastic.

7. An apparatus for cleaning surgical cautery tips comprising:
   a substantially non-compressible base having a top surface and a bottom surface, said base being resistant to penetration by sharp surgical instruments;
   a pad mounted on the top surface of the base and having an upper fibrous abrasive portion and a lower compressible portion, said lower compressible portion being located between the upper abrasive portion and the top surface of the base, said upper fibrous abrasive portion containing one or more elongated slits which penetrate the surface of the upper fibrous abrasive portion and which have a first end, a second end, opposing abrasive walls and an abrasive floor for cleaning a cautery blade having two sides and an edge by pressing the edge of the blade down between any two opposing abrasive walls at the first end deforming the floor and compressing the lower compressible portion to bring the opposing abrasive walls together against the sides of the cautery blade and then drawing the blade through the slit towards the second end to clean the cautery blade;

said base and said pad being constructed from materials suitable for sterilizing to permit the cautery tip cleaner to be used in surgery or for other medical procedures.

8. The apparatus of claim 7 in which said base is constructed from a hard plastic.

9. The apparatus of claim 7 additionally comprising a means for attaching the apparatus to a surface within easy reach of a user.

10. The apparatus of claim 9 in which said means for attaching the apparatus comprises adhesive attached to the bottom surface of the base.

11. The apparatus of claim 7 in which the compressible portion comprises sponge.

12. The apparatus of claim 7 wherein the fibrous abrasive portion comprises SCOTCHBRITE ®.

13. The apparatus of claim 7 wherein the fibrous abrasive portion is sufficiently thick so that if a cautery needle is pushed through said abrasive portion and withdrawn, any coagulum or debris attached to said needle will be substantially removed by the fibrous abrasive.

14. A method for cleaning cautery blades using only one hand in which a cautery blade having an edge and two sides is cleaned using a cautery tip cleaner comprising a compressible pad mounted on a substantially non-compressible base having a means for attaching the cautery tip cleaner to a surface within easy reach of a user, said compressible pad including an upper fibrous abrasive portion and a lower compressible portion located between the base and the upper abrasive portion, the upper abrasive portion including one or more elongated slits which penetrate the surface of the upper fibrous abrasive portion, each elongated slit having a first end, a second end, opposing abrasive walls and an abrasive floor, said method comprising:

attaching the cautery tip cleaner to a surface within easy reach of the user;

pressing the edge of the blade down between two opposing abrasive walls at the first end of an elongated slit, deforming the floor of the slit and compressing the lower compressible portion to bring the opposing abrasive walls together against the sides of the cautery blade;

drawing the blade through the slit towards the second end to clean the sides and the edge of the tip of the cautery blade.

* * * * *